United States Patent [19]

Sparks

[11] Patent Number: 4,604,804
[45] Date of Patent: Aug. 12, 1986

[54] CUTTING DEVICE FOR LIMB WRAPPINGS

[75] Inventor: Jimmy L. Sparks, Aiken, S.C.

[73] Assignee: Horse Health Products, Inc., S.C.

[21] Appl. No.: 707,905

[22] Filed: Mar. 4, 1985

[51] Int. Cl.[4] ............................................. B26B 29/00
[52] U.S. Cl. ........................................... 30/294; 30/162
[58] Field of Search ................. 30/294, 289, 286, 314, 30/162

[56] References Cited

U.S. PATENT DOCUMENTS

| | | | |
|---|---|---|---|
| 1,099,885 | 6/1914 | Peple | 30/294 |
| 1,187,615 | 6/1916 | Frees | 30/286 X |
| 1,813,868 | 7/1931 | Smiroldo | 30/294 |
| 2,705,833 | 4/1955 | Grantz | 30/294 |
| 3,751,806 | 8/1973 | Patrick | 30/294 |
| 3,831,274 | 8/1974 | Horrocks | 30/294 |
| 4,028,802 | 6/1977 | Houghton | 30/294 |
| 4,283,854 | 8/1981 | Austin | 30/314 |

FOREIGN PATENT DOCUMENTS 713763  7/1965  Canada .................................. 30/294

Primary Examiner—Jimmy C. Peters
Attorney, Agent, or Firm—Harlan P. Huebner

[57] ABSTRACT

A cutting device with a safety lip to prevent the end of a blade of the device from causing injury to a limb when a wrapping or bandage is being cut therefrom.

The device includes a handle and at one end there is mounted a cutting blade having a point and the point is covered by a blunt lip which engages the skin and will prevent injury as the blade is moved along the limb.

In addition, the end of the handle where the blade is mounted is concave and acts as a surface to prevent bunching of the wrappings being cut.

2 Claims, 12 Drawing Figures

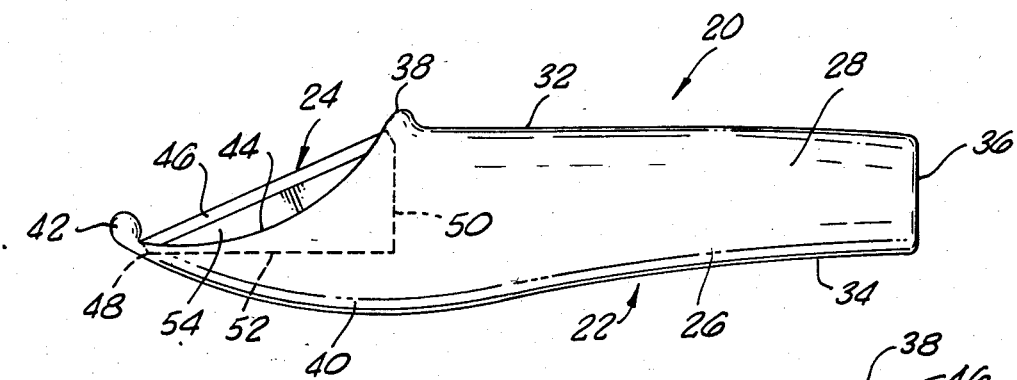
FIG. 1.
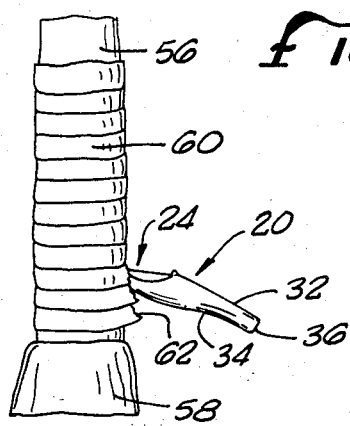
FIG. 3.
FIG. 2.
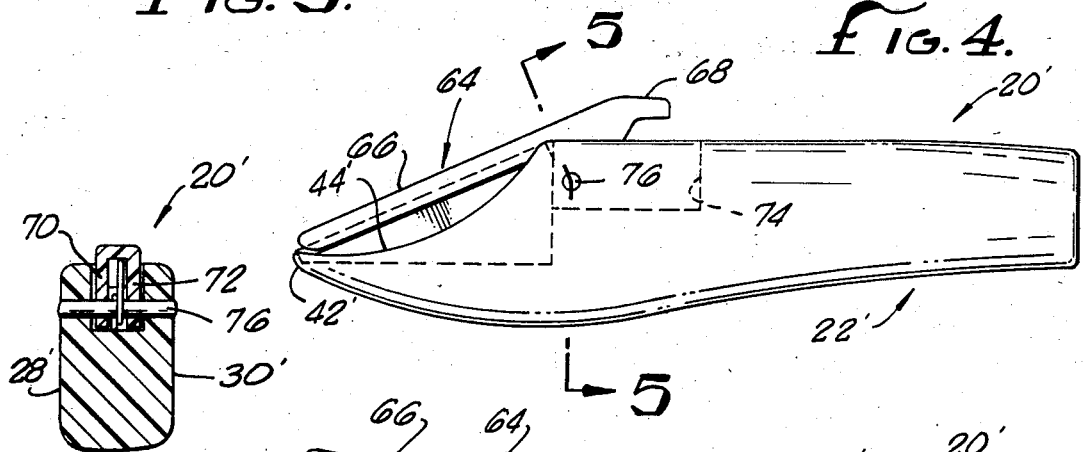
FIG. 4.
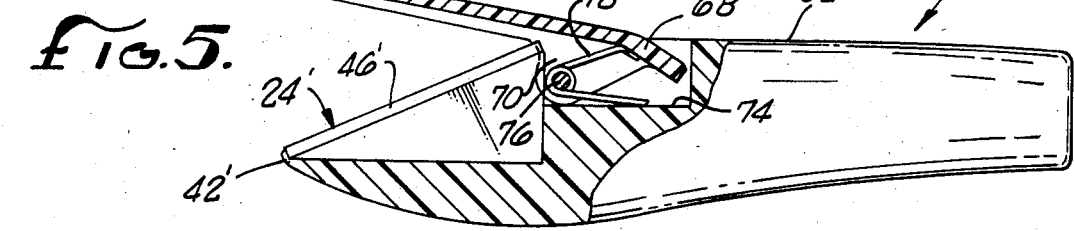
FIG. 5.
FIG. 6.

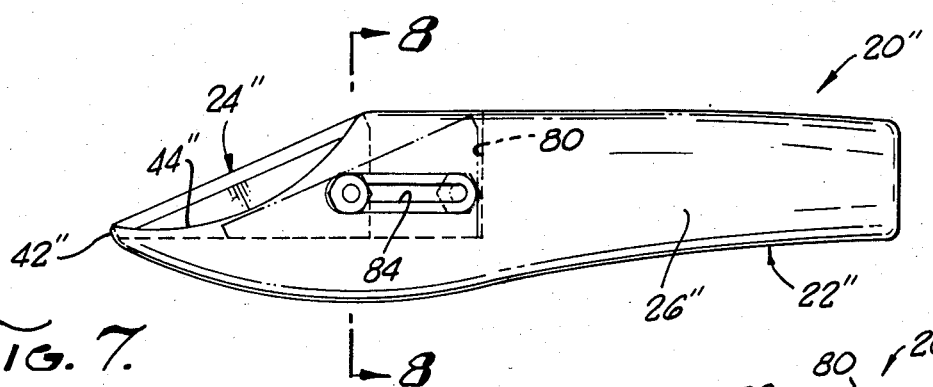
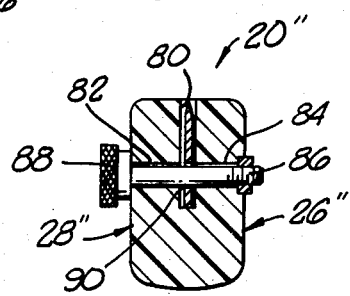
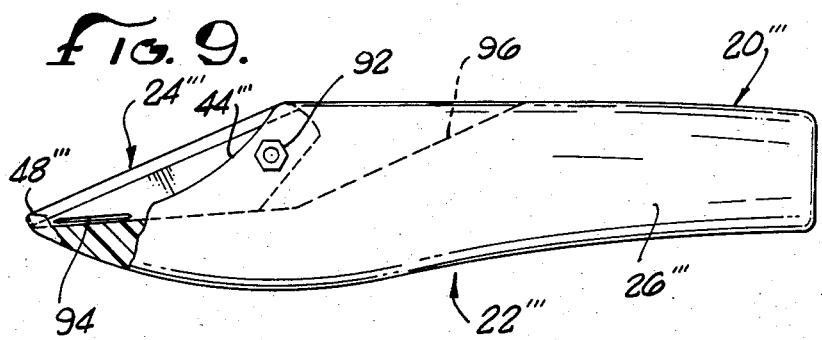
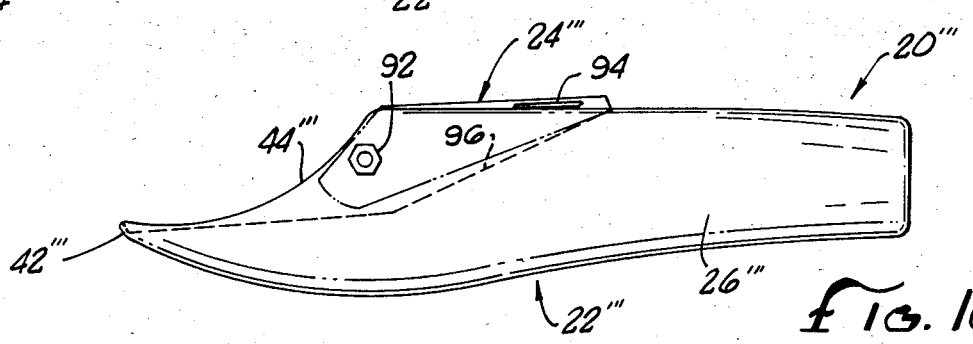
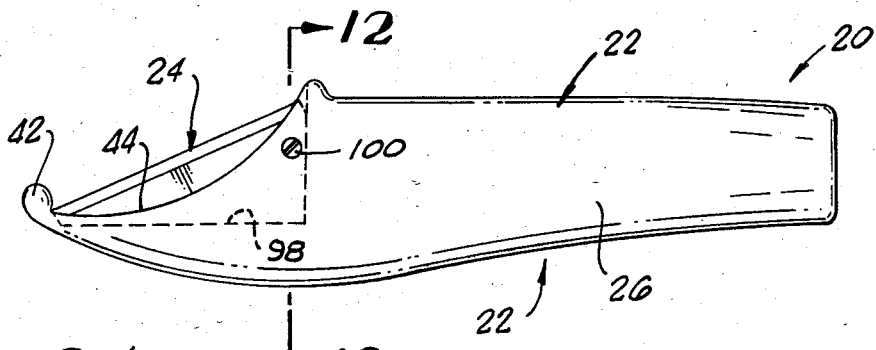
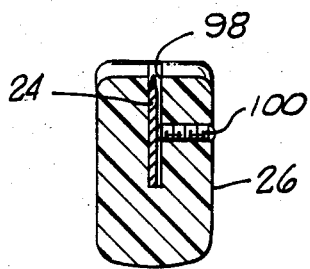

CUTTING DEVICE FOR LIMB WRAPPINGS

BACKGROUND OF THE INVENTION

When horses are groomed or prepared for competition usually their legs below the hock are wrapped with a continuous strip of flexible material such as cotton, paper, gauze, rubber, plastic or a product called "Vet Wrap". Also another form of wrapping called "Gelcast" is a gelatine type of product that is wetted, placed around the leg and allowed to partially dry.

The reason for the wrapping is to prevent injury to a horse's leg during competition or exercise.

Once the competition or exercise is concluded it is necessary to remove the wrapping and allow unrestricted movement of the leg.

Heretofore the wrappings have been removed by cutting the some upwardly or downwardly with a knife or scissors.

The problem with such removal is that the point of the knife or scissors can cut into the leg as it is being used. Horses after competition might be "flighty" and nervous and may not stand still for the removal of the wrappings.

Other than a knife or scissors the only other type of cutting instrument known that can accomplish removal of the bandage or wrapping is that defined in U.S. Pat. No. 3,888,002. However, the invention of that patent has the same disadvantages of a knife or scissors in that the blade has an exposed sharp point which can cause injury to the horse.

SUMMARY OF THE INVENTION

It is the purpose of the present invention to provide a safe cutting device to remove limb wrappings which will not injure the limb as the wrapping is removed.

While the invention to provide a safe cutting device is primarily directed to use with horse and animal legs, it may also be used to remove bandages and wrappings from humans as well.

Another object of the invention is to provide a handle and a cutting blade which comes to a point, but wherein the handle structure contains a blunt portion at the blade point whereby no injury can result from the cutting blade point.

A further object is to provide a safe-cutting device on either side of the blade to assume movement and separation of the wrapping during cutting so there is no bunching up or gathering of material to impair the cutting and removal.

These and other objects and advantages will become apparent from the following part of the specification wherein details have been described for the competence of disclosure, without intending to limit the scope of the invention which is set forth in the appended claims.

BRIEF DESCRIPTION OF THE DRAWINGS

These advantages may be more clearly understood from the following detailed description and by reference to the drawings in which:

FIG. 1, is a view in side elevation of the cutting device of FIG. 1;

FIG. 2 is an end view of the cutting device of FIG. 1;

FIG. 3, is an environmental view of the cutting device as it is cutting the wrapping surrounding the lower leg of a horse;

FIG. 4, is a view in side elevation of a modified form of the cutting device for limb wrapping including a hinged cover;

FIG. 5, is a view in cross section taken on line 5—5 of FIG. 4;

FIG. 6, is a view in side elevation partially in section of the cutting device for limb wrapping;

FIG. 7, is a view in side elevation view of a further modified form of the cutting device for limb wrapping including a retractable blade;

FIG. 8, is a cross-sectional view taken on line 8—8 of FIG. 7;

FIG. 9, is a view in side elevation of yet another form of cutting device for limb wrapping including a hingeable blade in an open position;

FIG. 10, is a view in side elevation of the cutting device for a limb wrapping of FIG. 9 with the hingeable blade in a closed position;

FIG. 11, is a view in side elevation of still another form of cutting device for limb wrapping including a replaceable blade attached therein; and FIG. 12, is a view in cross-section taken on line 12—12 of FIG. 11.

DETAILED DESCRIPTION OF THE PREFERRED EMBODIMENT

Specifically referring to FIG. 1 there is illustrated cutting device generally designated 20 including a handle member generally designated 22 and a cutting blade generally designated 24.

Preferably the handle 22 made from material such as plastic or wood includes an elongated portion 26 with generally parallel side walls 28 and 30, top 32 and bottom surface 34. From end 36 the top 32 may bow slightly upward and terminate at front upper end 38.

The bottom surface 34 extends forwardly from end 36 and is curved downwardly with a forward section 40 formed and then curved upward terminating in a protective lip 42.

Between the lip 42 and the end 36 the handle 22 is curved forming preferably a concave surface 44.

Mounted in the handle 22 and extending between the front forward end 38 and lip 42 is blade 24. The blade has tapered cutting edge 46 with a point 48 shown in dotted lines which is inserted within the lip 42. The blade is set in the handle and has a rear end 50 and bottom edge 52 shown in ghost lines. The blade 24 may be secured within the handle by adhesive or any well known means.

Further, as best seen in FIG. 1, portions of the sides 52 and 54 of the blade 24 are exposed between the cutting edge 46 and concave surface 44.

FIGS. 4, 5 and 6 show a modified form of cutting device 20' wherein the handle member 22' is similar to the device of FIG. 1. A distinction over the FIG. 1 embodiment resides in the addition of a blade edge cover generally designated 64.

The cover 64 includes an elongated sheath 66 which is an inverted U and extends around the cutting edge 46'. The cover 64 also includes a thumb release 68 which includes a pair of spaced apart downwardly extending ears 70 and 72 mounted in a recess 74 cut into the top 32'. There is preferably provided a pivot pin 76 which extends through the handle sides 28' and 30' and ears 70 and 72.

In order to make the cover 64 return to the closed position of FIG. 4 once the thumb release 68 is released a tension spring 78 is provided between ears 70 and 72.

When it is desired to use the device 20', the cover 64 is opened as in FIG. 6 and the blade 24' can then be used to cut.

In FIGS. 7 and 8 a second embodiment of the cutting device 20" is a retractable cutting blade 24".

The handle includes a slot 80 extending inward from the lip 42" as shown in dotted lines in FIG. 7.

In order to present the retractable blade 24" there are aligned slots 82 and 84 extending through respective sides 26" and 28" of handle 20". Mounted in the slots 26" and 28" is a bolt 86 with a knurled handle 88 which also extends through a bore 90 in the blade.

When the blade 24" is to be ready for use the knearled handle is moved forward as in FIG. 7 and backward to retract as seen in ghost lines in FIG. 7.

FIGS. 9 and 10 illustrate still another modification where the blade 24''' is retractable into the handle 22''' as a jack knife would do. The blade 22''' is hinged by a pin 92 extending through the blade and sides 26''' and 28'''.

On the blade 24''' adjacent point 48''' is a nail groove 94 by which the blade may be moved from the open position of FIG. 9 to the closed position within the slot 96 as seen in FIG. 10.

Finally, another embodiment shown in FIGS. 11 and 12 is identical to FIG. 1 with the exception that the blade 24 is replaceable and not permanently secured in the handle 22.

The blade 24 rests in a slot 98 in the handle and a set screw 100 passes through side 26 into the slot 98 and bears against the blade 24 to hold it in place.

The invention and its attendant advantages will be understood from the foregoing description and it will be apparent that various changes may be made in the form, construction and arrangements of the parts without departing from the spirit and scope thereof or sacrificing its material advantages, the arrangements hereinbefore described being merely by way of example. I do not wish to be restricted to the specific forms shown or uses mentioned, except as defined in the accompanying claims, wherein various portions have been separated for clarity of reading and not for emphasis.

I claim:

1. A cutting device for removing limb wrappings wherein said device comprises:

a handle including an elongated portion having a elongated axis and an outer end, said elongated portion including top and bottom surfaces projecting from said end and said top surface terminating in a front upper end, and said bottom surface curving upwardly and extending forwardly of said front upper end terminating in a protective lip below and forwardly of said front upper end;

a generally concave biasing surface extending from said protective lip to said front upper end;

a cutting blade having generally parallel sides mounted in said handle within said biasing surface and extending at an angle to said elongated axis from a point inwardly of said protective lip adjacent said front upper end, whereby said protective lip is slightly outward of and elevated above said point of intersection of said blade with said biasing surface to afford protection from said blade; and said lip portion adapted to enter between said limb and said wrappings at any reasonable angle without cutting injury to said limb and said cutting blade engages said wrappings and upon movement cuts said wrappings with said wrappings on each side of said blade being biased on said biasing surface away from each other to prevent interference with said cutting.

2. A cutting device as defined in claim 1 wherein said biasing surface tapers away from each of said sides of said blade.

* * * * *